(12) United States Patent
Henion et al.

(10) Patent No.: US 8,546,752 B2
(45) Date of Patent: Oct. 1, 2013

(54) SOLID-PHASE EXTRACTION (SPE) TIPS AND METHODS OF USE

(75) Inventors: John D. Henion, Trumansburg, NY (US); Thomas Kurz, Ithaca, NY (US)

(73) Assignee: Advion Inc., Ithaca, NY (US)

(\*) Notice: Subject to any disclaimer, the term of this patent is extended or adjusted under 35 U.S.C. 154(b) by 212 days.

(21) Appl. No.: 12/960,037

(22) Filed: Dec. 3, 2010

(65) Prior Publication Data

US 2011/0133077 A1 Jun. 9, 2011

Related U.S. Application Data

(60) Provisional application No. 61/267,251, filed on Dec. 7, 2009.

(51) Int. Cl.
*H01J 49/26* (2006.01)

(52) U.S. Cl.
USPC .......................................... 250/288; 250/282

(58) Field of Classification Search
USPC .......................................... 250/281, 282, 288
See application file for complete search history.

(56) References Cited

U.S. PATENT DOCUMENTS

| | | | |
|---|---|---|---|
| 6,274,094 | B1 | 8/2001 | Weller, III et al. |
| 6,566,145 | B2 | 5/2003 | Brewer |
| 6,770,246 | B1 | 8/2004 | Husek |
| 7,740,763 | B2 | 6/2010 | Marcus et al. |
| 7,749,447 | B1 | 7/2010 | Sauter, Jr. |
| 7,776,615 | B2 | 8/2010 | Yuka et al. |
| 7,927,486 | B2 | 4/2011 | Shah et al. |
| 8,105,513 | B2 | 1/2012 | Bonn et al. |
| 8,124,727 | B2 | 2/2012 | Shukla et al. |
| 2005/0276727 | A1\* | 12/2005 | Pawliszyn et al. ............. 422/99 |
| 2006/0216206 | A1 | 9/2006 | Hudson et al. |
| 2008/0090295 | A1\* | 4/2008 | Feuerstein et al. ............. 436/54 |
| 2008/0119637 | A1 | 5/2008 | Gjerde et al. |
| 2010/0003683 | A1 | 1/2010 | Sarofim et al. |
| 2010/0081209 | A1 | 4/2010 | Brewer |
| 2011/0111443 | A1 | 5/2011 | Nishimura et al. |
| 2011/0136251 | A1\* | 6/2011 | Astle ............................ 436/178 |
| 2012/0175368 | A1 | 7/2012 | Dimson et al. |

\* cited by examiner

*Primary Examiner* — Nicole Ippolito
(74) *Attorney, Agent, or Firm* — Fish & Richardson P.C.

(57) ABSTRACT

Methods and systems for extraction of analytes from samples for analysis using mass spectrometers are described herein.

15 Claims, 9 Drawing Sheets

SOLID-PHASE EXTRACTION (SPE) TIPS AND METHODS OF USE

CROSS-REFERENCE TO RELATED APPLICATIONS

This application claims the benefit under 35 U.S.C. §119 (e) of U.S. Application Ser. No. 61/267,251, filed on Dec. 7, 2009, which is incorporated by referenced herein.

TECHNICAL FIELD

Methods and systems for extraction of analytes from samples for analysis are described herein.

BACKGROUND

Mass spectrometry is an analytical process that identifies the chemical composition of a compound or sample based on the mass-to-charge ratio of charged particles derived from the compound or sample. In general, in mass spectrometry, a sample undergoes ionization to form charged particles (ions). The ratio of mass-to-charge of the particles is determined by passing them through electric and/or magnetic fields in a mass spectrometer.

In some mass spectrometer systems, molecules can be analyzed in a quadrupole mass spectrometer using "electrospray" ionization to introduce the ions into the spectrometer. In electrospray ionization a spray needle may be positioned near to the entrance orifice of a quadrupole, magnetic, ion trap, Fourier transform mass spectrometer (FTMS), orbitrap, or time-of-flight (TOF) mass spectrometer, or close to the entrance of a capillary leading to a vacuum entrance orifice of the quadrupole or other type of mass spectrometer. A dilute solution, including the molecules of interest, is pumped through the electrospray needle or emitter and an electric potential between the needle or emitter orifice and a vacuum orifice (e.g., a reference electrode) leading to the mass analyzer forms a spray ("electrospray") of the solution.

SUMMARY

The invention relates to methods and systems for extraction of analytes from samples for analysis using mass spectrometers.

In certain aspects, a method of extracting analytes from a sample includes introducing a solvent into an extraction tip; causing the solvent to contact a solid phase extraction (SPE) or chromatographic packing material within the extraction tip; dispensing the solvent to contact a surface of a sample outside of the extraction tip; and aspirating the eluting solvent and dissolved analytes into the extraction tip from the surface of the sample through a first end of the extraction tip such that the analytes are retained in the SPE packing material in the extraction tip by applying a vacuum at a second end of the extraction tip.

In some aspects, a method of extracting analytes from a sample includes positioning the sample within an extraction tip; introducing a solvent to a first end of the extraction tip; causing analytes within the sample to dissolve in the solvent; causing the solvent to contact a solid phase extraction (SPE) packing material within the extraction tip; eluting the analytes retained by the SPE packing material; and causing the dissolved analyte to exit from a second end of the extraction tip.

Embodiments can include one or more of the following features.

In some embodiments, the method includes repeating the steps of dispensing, applying and aspirating at different locations of the sample.

In some embodiments, the method includes repeating the steps of dispensing, applying and aspirating at the same location on the sample.

In some embodiments, the method includes interfacing the extraction tip to an automation device to deliver the extraction tip to an ion sprayer; and directing ions from the ion sprayer to a mass analyzer.

In some embodiments, the ion sprayer is an electrospray ionization source having multiple openings through which the extraction tip can singularly or in multiple deliver the analyte.

In some embodiments, the method includes aligning the extraction tip to be in close proximity to the sample.

In some embodiments, the first end of the extraction tip has a smaller diameter than the second end.

In some embodiments, a diameter of the first end is between 400 μm to 1200 μm and a diameter of the second end is between 1 to 10 mm.

In some embodiments, the sample includes a tissue slice.

In some embodiments, the sample comprises a dried blood spot card.

In some embodiments, dispensing the solvent includes dispensing microliters of eluting solvent from the first end of the extraction tip to contact the sample.

In some embodiments, the SPE packing material includes a material suitable for Hydrophilic Interaction Liquid Chromatography (HILIC).

In some embodiments, the solvent is a normal phase eluting solvent.

In some embodiments, the normal phase eluting solvent includes methanol or acetonitrile.

In some embodiments, the solvent is introduced to the extraction tip via the first end.

In some embodiments, the eluting solvent forms a micro liquid junction between the first end of the extraction tip and the sample surface.

In some embodiments, aspirating the solvent and dissolved analytes into the extraction tip via the first end of the extraction tip includes extracting multiple analytes from the sample.

In some embodiments in which the sample is positioned within the extraction tip, the first end has a larger diameter than the second end.

In general, in some examples, a method for analyzing a sample includes aspirating solvent from a solvent reservoir to fill the lower end of the extraction tip, locating the SPE tip over and very close to a sample surface (e.g., a dried blood spot card), dispensing a very small micro liquid junction droplet to perform a micro extraction of the sample surface. The micro droplet can subsequently be aspirated up into the SPE packing followed by placement of the SPE tip against the chip-based ion sprayer whereupon electrospray mass spectrometry analysis is performed.

The details of one or more embodiments of the invention are set forth in the accompanying drawings and the description below. Other features, objects, and advantages of the invention will be apparent from the description and drawings, and from the claims.

Advantages of the disclosed systems, devices and methods can include providing an integrated platform that directly extracts analytes from sample surfaces (e.g., dried blood spot cards), traps the extracted analytes in an extraction tip, and performs some degree of chromatography or separation of the analytes when eluted with an eluting solvent from the extraction tip. The disclosed systems and devices are configured to interface with automation devices for high-speed, high throughput mass spectroscopic analysis of samples, in which a single extraction tip is used to collect the sample and provide the sample to a mass spectrometry device.

DESCRIPTION OF DRAWINGS

Like reference symbols in the various drawings indicate like elements.

DETAILED DESCRIPTION

Mass spectrometry systems can identify the chemical composition of a compound (e.g., an analyte) contained in a sample based on the mass-to-charge ratios of ions derived from the compound. One method of providing a sample to a mass spectrometry system is to extract analytes from the sample and elute the analytes through a chromatography column having an outlet in fluid communication with the mass spectrometry system. For example, an extraction tip (e.g., a solid phase extraction (SPE) tip) can deliver a solvent onto a sample contained on or within a surface such that analytes from the sample become dissolved in the extraction solvent, collect the solvent and the dissolved analytes, and provide the solvent and the analytes as a sample solution to the mass spectrometry system.

Figure 1A:
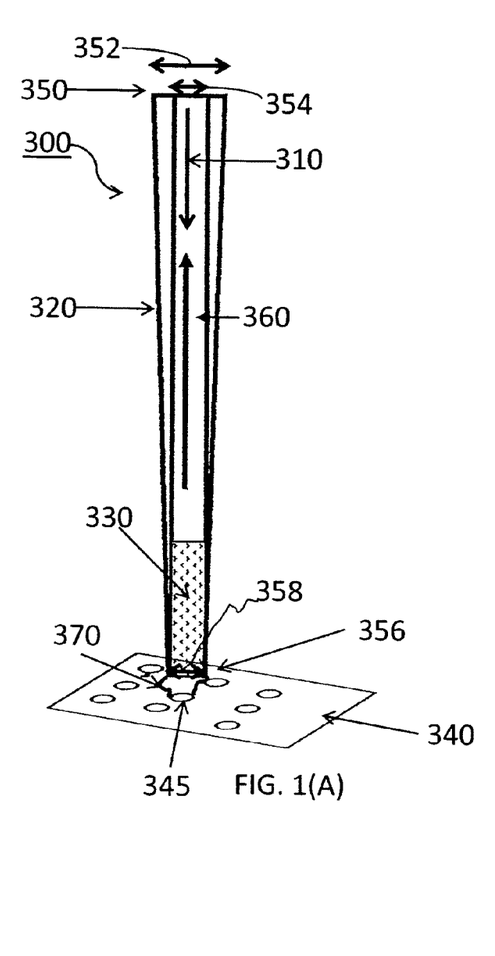
FIG. 1A shows a solid-phase extraction tip and a sample card.

FIG. 1A is a schematic representation of an extraction tip 300. Extraction tip 300 can be used to extract one or more analytes directly from a surface of a sample plate 340. Extraction tip 300 is formed of a hollow cone or cylindrical shaped body 320 with a narrow inside diameter. Solid-phase extraction (SPE) packing material 330 is arranged near one end 356 of the extraction tip 300 (e.g., within about 10 µm, within about 5 µm, within about 2 µm, or flush with but not extending beyond the end 356). The SPE packing material is used to separate compounds via a chromatographic process that are dissolved or suspended in a liquid mixture from other compounds in the mixture based on their physical and/or chemical properties. In particular, the difference between the affinity of solutes dissolved or suspended in the solvent (e.g., the mobile phase) for the SPE packing material (e.g., the stationary phase) through which the sample is passed is used to separate a mixture into its components. The desired analytes are separated from the mixture and the analytes may reside either in the mobile phase or in the stationary phase.

Figure 1B:
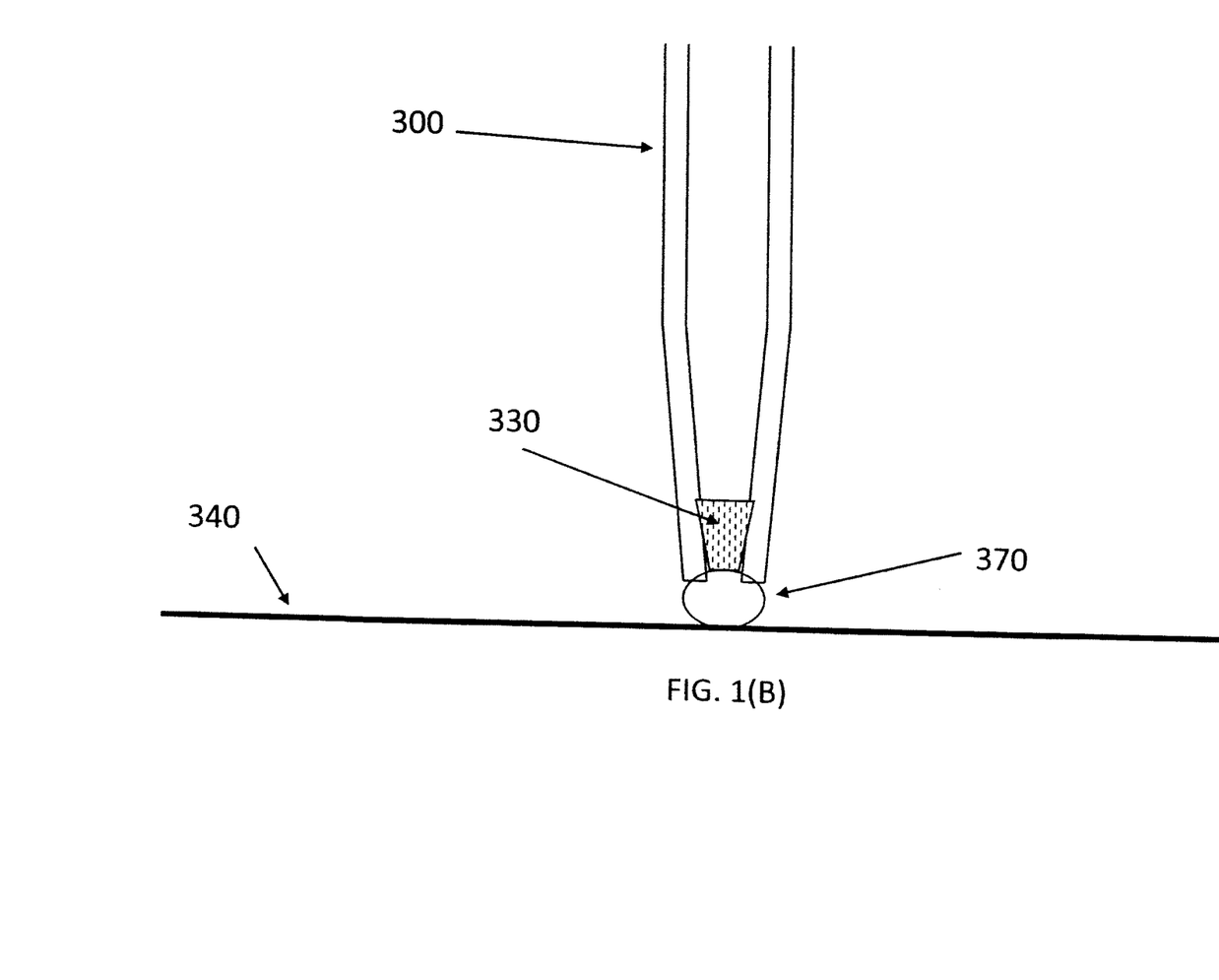
FIG. 1B shows a solid-phase extraction tip and a sample card.

During use, the end 356 of extraction tip 300 is placed within a solvent reservoir containing an abundance of the desired extraction/elution/spray solvent. This first step aspirates an aliquot of the extraction solvent (1 µL to 20 µL, for example) which loads and wets the SPE packing material contained within the SPE tip. Introducing the solvent into the SPE packing material in the extraction tip 300 readies the extraction tip for extraction of analytes from a sample surface. The now wetted SPE tip is removed from the solvent repository and repositioned in close proximity to the sample plate or surface 340 (e.g., a dried blood spot card, tissue slice or other surface containing a sample). In some examples, the sample plate or surface 340 can include multiple sample spots 345 (e.g., dried blood spots) or areas containing analytes of interest. After the extraction tip is in the desired location, the eluting solvent is slowly dispensed to flow from the smaller diameter end 356 of the extraction tip 300 through the SPE packing material and onto the sample spot 345 as indicated by arrow 310. A small volume, for example, 1-50 microliters, of eluting solvent can be dispensed from the end 356 of the extraction tip 300 and onto the sample surface. The eluting solvent forms a micro liquid junction 370 between the end 356 of the extraction tip and the surface of the sample spot 345 (e.g., as shown in FIG. 1B). Once in contact with the spot 345, the eluting solvent dissolves analytes from the sample spot 345. A partial vacuum is applied to the larger diameter end 350 of the extraction tip 300 to aspirate the eluting solvent and the dissolved analytes from the sample spot 345 into the extraction tip 300 in the direction represented by arrow 360. Exemplary vacuum ranges used for aspirating the dissolved analytes and eluting solvent into the extraction tip 300 can be between about 50 Torr to about 750 Torr. (e.g., from about 100 Torr to about 500 Torr, about 700 Torr).

In some embodiments, body 320 is made of polypropylene. In some embodiments, extraction tip 300 can include a pipette tip used for aliquoting liquids in a laboratory setting. In other embodiments 300 may be constructed of metal as in a Luer pipette tip or polyether ether ketone (PEEK) or other chemically resistant materials which may be used to accomplish the described process.

In the example shown in FIG. 1A, the end 356 has a smaller diameter than the larger diameter end 350. In some embodiments, the end 350 of the extraction tip 300 has an outer diameter 352 and an inner diameter of 354 that is larger than the end 356 which has a reduced inner diameter 358. The larger diameter end 350 of the extraction tip allows the extraction tip 300 to be connected to a mandrel of a solvent supply system as well as a source of partial vacuum for aspiration of liquids while the smaller diameter end allows more controlled dispensing and aspiration of the solvent to and from the sample surface. The outer diameter 352 of the larger diameter end 350 may be from about 1 mm to 10 mm (e.g., between 2-8 mm, between 3-6 mm), and the inner diameter 354 of the larger diameter end 350 may be from about 0.1 mm to 4 mm (e.g., between 0.5-3 mm, between 0.2-2 mm). In some embodiments, the smaller diameter end 356 has an inner diameter that is between about 100 µm to about 700 µm and an outer diameter that is between about 600 µm to about 1200 µm (e.g., the inner diameter is between 300 µm to 500 µm, the inner diameter is between 350 µm and 450 µm, the outer diameter is between 700 µm to 1100 µm, the outer diameter is between 800 µm and 900 µm).

In comparison to extraction techniques in which the extraction of analytes is performed using wet chemistry to prepare samples (e.g., in multi-well plates) before the samples are loaded onto an extraction tip, the use of the extraction tip described herein can provided various advantages. Directly extracting analytes from a sample surface can be advantageous, and particularly so in trace analysis, because the sample comes into contact with fewer surfaces. Every additional surface involved in sample preparation and/or extraction can potentially lead to loss of analytes. Reducing the loss of analytes is advantageous because, in trace analysis, the concentrations of analytes can be in the parts per billion (ppb) range, thus a small loss can lead to difficulty in detection. The apparatus and methods described herein also allow the extraction and chromatographic separation to be done on a single device followed by the extraction tip then directly communicating with the mass spectrometry system. Additionally, the methods and systems described herein limit the amount of solvent used in the extraction of the analytes which can increase the concentration of analytes in the solvent resulting in lower levels of detection; e.g. higher sensitivity.

As noted above, the extraction tip 300 includes an SPE packing material. In general, the packing material serves to retain analytes and/or perform chromatographic separation. The amount of packing material can vary based on the intended application for the tip. For example, the tip can include packing materials 330 packed to a length of a few tens of millimeters, to a few millimeters and even to a few centimeters, depending on the capacity required for extracting and retaining the desired amount of analytes from a sample. For example, if the volume of extracted analytes is large, if the sampling area over which the extraction is carried out is large, if the extraction mixture has a large number of components, or if the differences between the affinity for the mobile phase and the stationary phase between different components in the mixture is small, then the amount of packing material may be greater. SPE packing material 330 is arranged within the extraction tip such that it is flush (e.g., within about 10 μm, within about 5 μm, within about 2 μm to an edge of the extraction tip) with respect to the end 356 of the extraction tip and that no packing material protrudes from (e.g., extends past) the end 356. In some embodiments, the SPE packing material can be formed of packed particulates, each of the particles can have sizes between 1.7-50 μm (e.g., between 5 μm to 40 μm, about 10 μm. The packing material can be formed in the tip using a variety of methods. In one particular example, a slurry of particulate SPE packing material can be prepared at balanced density such that the particulates are suspended evenly within the solvent. This slurry can be introduced into the extraction tip. Once the balanced density mixture is introduced into the extraction tip, the solvents are removed, yielding the packed extraction tip.

In some examples of extraction tips which are made of materials that are substantially smooth (e.g., plastic), in order to ensure that the SPE packing material is secured in the extraction tip, a sintered plug or frit may be placed at an open end (e.g., the end closer to end 356) of the SPE packing material, at the surface where the extraction solvent first contacts the sample surface. The sintered plug or frit may be sized to fit snuggly within the inner diameter of the extraction tip. Friction between the unitary piece of sintered plug and the extraction tip helps to ensure that the SPE packing material stays packed within the extraction tip by blocking the dispersion of packing material.

In some embodiments, the SPE packing material arranged in the extraction tip 300 is formed as a monolithic formation which is a porous rod or substrate which can also act as a chromatographic support. The rod can have a length of between 1-3 cm (e.g., between 1.5-2.5 cm, between 0.5 to 5 cm) and a diameter from about 0.25 mm to about 0.9 mm (e.g., between 0.4 mm to 0.7 mm, between 0.45 to 0.55 mm). In some embodiments, an aspect ratio (the ratio of the rod length to the rod diameter) of the rod can be greater than 10:1 (e.g., greater than 10:1, greater than 15:1, greater than 20:1, greater than 30:1). In general, the diameter of the rod is substantially the same as the inner diameter of the end 356. Such a monolithic rod may include a polymer that is formed either by heat treatment of precursor materials (e.g., monomer materials) or by light treatment of a suitable light-activated mixture of precursor material. These monolithic rods have a suitable porosity (e.g., a porosity of 0.5 μm measured using standard imaging techniques to 3 μm or 0.75 μm to 2 μm or possibly a preferred pore size of 1 μm) for chromatographic separation of analytes. In general, the SPE material is formed such that no cavity (e.g., gaps having a dimension larger than 0.01 μm, gaps larger than 0.05 μm) is formed between the SPE packing material and the inside surface or wall of the SPE tip, which may decrease the efficacy of the chromatographic separation of analytes.

The extraction tip 300 provides an integrated platform that directly extracts analytes from sample surfaces (e.g., dried blood spot cards), traps the extracted analytes in an extraction tip, and performs some degree of chromatographic separation of the analytes when eluted with an eluting solvent from the extraction tip 300. The disclosed systems and devices are configured to interface with automation devices for high-speed, high-throughput mass spectroscopic analysis of samples, in which a single extraction tip is used to collect the sample and provide the sample to a mass spectrometry device. As such, an automated process using a single tip can simplify the extraction and analysis of samples, reduce the costs associated with additional hardware when multiple tips are used to access unique areas of a sample surface, and increase the speed of the extraction and analysis process.

It is believed that the use of a single tip for each individual sample can provide various advantages such as increased sensitivity due to reduced sample loss and higher sample solution concentrations due to low volume solvent extractions, eliminate carryover or cross-contamination between different samples since a different SPE tip is used for each and every sample, and ease of automation with existing systems (e.g., retrofitting to mass spectrometer systems).

FIG. 1B shows another schematic view of the solid-phase extraction tip and a sample surface. The micro liquid junction 370 is formed between the small diameter end of the extraction tip 300 and the sample surface 340. In general, the micro liquid junction 370 is formed of a very small volume of extraction/elution solvent (e.g., between 0.1-10 μL, between 2-6 μL, between 1-5 μL). The micro liquid junction 370 extends from the end of the extraction tip to the surface of the sample.

Figure 2:
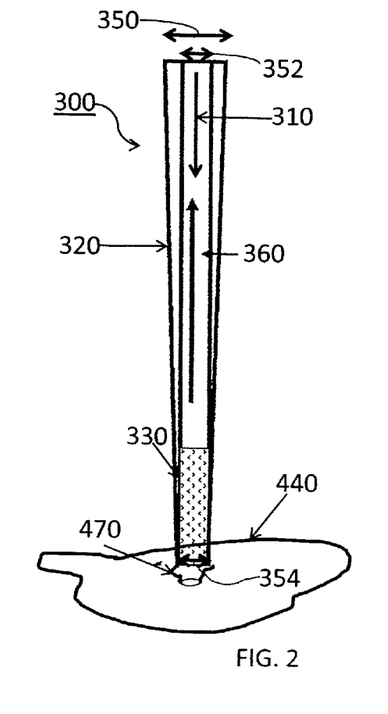
FIG. 2 shows a solid-phase extraction tip and a tissue slice.

While in the example described above the tip was described as being used to extract analytes from a dried blood spot on a dried blood spot card similar tips can be used to extract analytes from other types of samples. For example, FIG. 2 shows an embodiment in which extraction tip 300 is used to directly extract one or more analytes from a thin tissue slice 440. In this case, a micro liquid junction 470 is formed between the end 356 of extraction tip 300 and the tissue slice 440. For example, tissue slice 440 may be between 10-150 micrometers thick (e.g., 50 nm thick, 80 nm thick, 140 nm thick) slice of tissue sample. In such applications, extraction tip 300 helps to clean up and concentrate the sample components in addition to extracting the analytes from the thin tissue matrix. The samples (e.g., the extracted analytes) are cleaned when the various extracted analytes retained by the SPE packing material are chromatographically separated by the solvent eluting the column of SPE packing material. In general, the extraction tip 300 can be used to extract analytes from other types of sample surfaces besides DBS and tissue slices.

Figure 3:
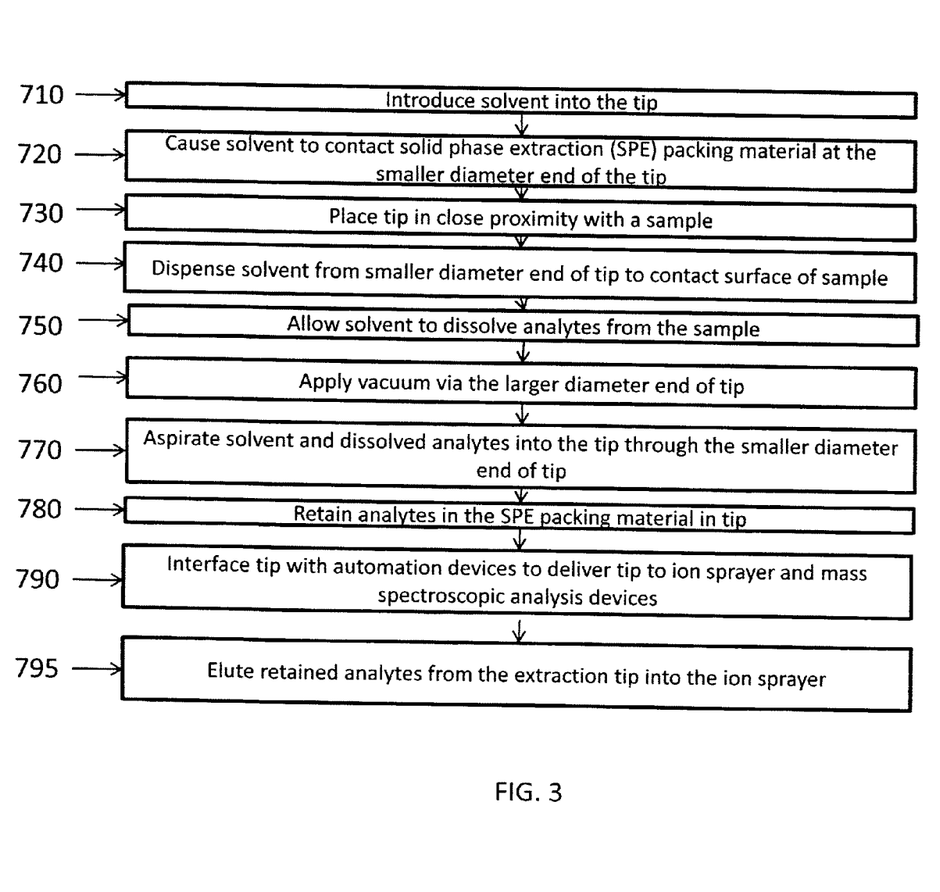
FIG. 3 is a flow chart of an extraction process.

FIG. 3 shows a flow chart of an exemplary extraction process. In general, in this process, a single extraction tip is used to extract analytes from a sample and provide the analytes to a mass spectrometry system for analysis. More particularly, different extracted analytes retained by the SPE packing material contained in the extraction tip are separated into components when the tip is eluted with a solvent.

In step 710, the eluting solvent is introduced into the extraction tip 300. In some examples, the solvent is introduced into the tip by aspiration of solvent from a solvent reservoir. This can be accomplished by immersing the smaller diameter end 356 of the extraction tip 300 below the surface of a solvent followed by partial suction in the direction of arrow 360 shown in FIG. 1A. In other examples, the solvent can be introduced into the extraction tip from the large diameter end of the extraction tip. The eluting solvent can be selected based on the SPE packing material contained within the extraction tip and the estimated polarity of the analytes which may be extracted from the sample matrix. In some embodiments, the SPE packing materials and the eluting solvent can consist of a hydrophilic interaction liquid chromatography (HILIC) system, a type of normal phase liquid chromatography which requires relatively high percentages of organic solvents for effective elution of analytes. In some embodiments, eluting solvents (e.g., the mobile phase) with high organic solvent content such as methanol and acetonitrile are used. The larger diameter end of the extraction tip is adapted to connect with a mandrel of a solvent supply system to provide the partial aspiration vacuum needed to aspirate the solvent into the extraction tip.

While introducing the solvent into the extraction tip, the solvent contacts the solid phase extraction packing material 300 arranged at the smaller diameter end of the tip in step 720. The elution solvent wets the column of SPE packing material contained within the extraction tip. The amount of packing material used within the extraction tip can be based on the quantity of analytes that need to be retained and/or the extent of chromatography anticipated to separate the components of the extracted sample.

In step 730, the extraction tip 300 is placed in close proximity to a sample. The eluting solvent is dispensed from the smaller diameter end of the tip and contacts the surface of the sample in step 740 to form a micro liquid junction between the sample surface and the SPE tip 356. In general, 0.5-10 microliters (μL) of eluting solvent (e.g., between 1-8 μL, between 2-6 L, between 1-5 μL) is dispensed from the extraction tip 300 onto a sample.

In step 750, the eluting solvent dissolves and hence extracts analytes from the sample. For example, the solvent may remain on the sample for a period of time to allow dissolving of analytes. A partial vacuum is applied via the larger diameter end of the tip in step 760 to aspirate solvent and the dissolved analytes into the extraction tip through the smaller diameter end of the tip. The larger diameter end of the extraction tip is connected through a mandrel of a vacuum system to lower the pressure within the extraction tip. A partial but sufficient vacuum is applied to aspirate the eluting solvent and dissolved analytes contained within the micro liquid junction into the extraction tip.

The aspirated analytes are retained in step 780 within the SPE packing material. The extraction tip can then be interfaced with automation devices to deliver the tip to an ion sprayer and mass spectroscopic analysis devices in step 790. In step 795, the retained analytes are eluted from the extraction tip and directed towards the ion sprayer to prepare analytes ions for mass spectroscopic analysis.

In some embodiments, steps 730 to 780 can be repeated before the extraction tip is delivered to the ion sprayer and mass spectroscopic analysis devices. The cycling sequence of dispensing eluting solvent, aspirating the eluting solvent and dissolved analytes back into the extraction tip can be repeated multiple times at a particular sample location to increase the concentration and/or amount of analytes sampled. In some embodiments, steps 730 to 780 are repeated as the extraction tip 300 is translated across various sample locations to extract analytes from different locations of the sample. In this manner, a larger aggregate sample surface is sampled using extraction tip 300.

The tips described herein can be used with various mass spectrometry systems and analysis systems. For example, ion mobility spectrometry systems coupled to a mass spectrometry system, the mass spectrometry system may include a sector instrument, a time-of-flight tube, a quadrupole mass filter, a three-dimensional quadrupole ion trap, a linear quadrupole ion trap, an orbitrap mass spectrometer, or Fourier transform ion cyclotron resonance instrument.

While step 710 as described above introduces the solvent into the extraction tip 300 via the smaller diameter end 356, in some embodiments, the solvent can also be introduced via the larger diameter end 350, as detailed below in reference to FIGS. 7 and 8.

The introduction of solvents from the smaller diameter end 356 may provide advantages. For example, a smaller amount of solvent can be introduced to wet the SPE packing material and then dispensed to dissolve analytes from the sample, minimizing the amount of dilution experienced by the dissolved analytes. Electrospray mass spectroscopy is a concentration-sensitive technique, and performance may be enhanced if the sprayed sample is more concentrated. Furthermore, a shorter cycle time can be achieved between analyses of different samples, thereby increasing throughput of the system, because a smaller amount of solvent is introduced into the extraction tip. In some other examples, introducing the solvents from the larger diameter end may provide additional advantages. For example, the tip will not be placed in contact with the solvent repository reducing the likelihood of cross contamination between the tip and the solvent reservoir.

Figure 4:
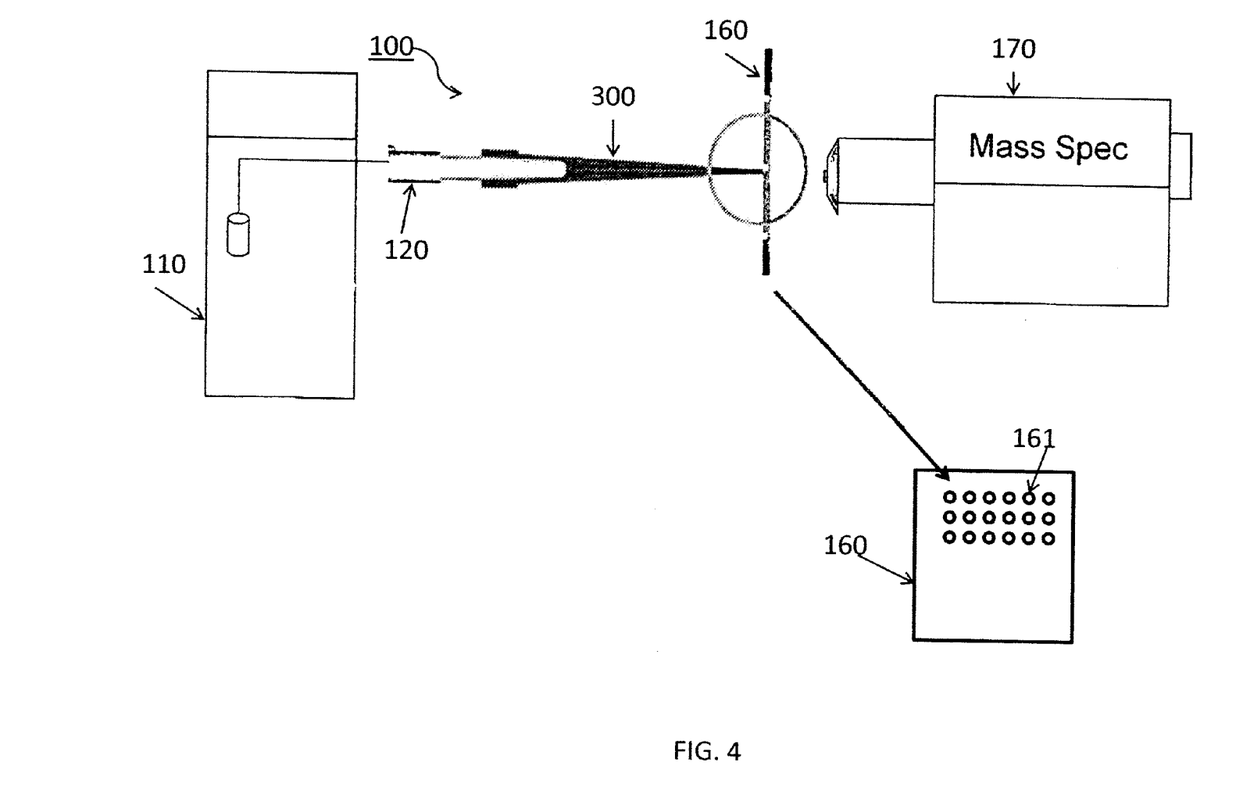
FIG. 4 shows a mass spectrometry system coupled with a solvent delivery system, the SPE extraction tip system and a microfluidic chip-based electrospray system.

FIG. 4 shows an exemplary mass spectrometry system 100 used to identify the chemical composition of a compound based on the mass-to-charge ratio of charged particles derived from the compound. The mass spectrometry system 100 includes a solvent delivery system 110 that provides appropriate elution solvents, usually of high organic solvent content, to the extraction tip 300. The elution solvent is selected based on the chosen SPE packing material and the analyte polarities. A mandrel 120 is used to connect the extraction tip 300 to the solvent delivery system 110. The solvent delivery system 110 may also include a means to provide a partial vacuum to the extraction tip 300 via a connection through the mandrel 120. The solvent delivery system 110 can be, for example, liquid chromatograph such as a Waters nanoACQUITY, an Eksigent micro High Performance Liquid Chromatography (HPLC) system, or a Shimadzu liquid chromatograph equipped with a split flow arrangement with a reduced flow of mobile phase directed to a robot. The robot may be a system such as the NanoMate™ or TriVersa NanoMate™ (Advion BioSystems, Ithaca, N.Y. USA) equipped with the mandrel 120, which is capable of picking up a pipette tip or SPE Tip from a multi-tip rack (e.g., 96 well plate, 384 well plate, 1536 well plate.). In some embodiments, the mandrel is a tapered metal rod having an inner diameter of, for example, from about 1 mm to about 5 mm. (e.g., about 2 mm, about 4 mm ,about 6 mm, about 10 mm).

During use, the robot may deliver the extraction tip 300 to the inlet surface of a microfabricated ESI chip 160 which houses a multitude of ESI emitters/electrospray nozzle sprayers 161. The end 356 of the extraction tip is aligned and positioned at an opening of the nozzle sprayers 161. Thus, during use a solvent is provided from the system 110 through the mandrel 120 and through the end 350 of the extraction tip. As the solvent passes through the SPE packing material, the analytes retained therein are dissolved in the solvent. Fluidic or hydrostatic pressure from the solvent delivery system advances the eluting solvent or mobile phase, and the dissolved analytes to the end 356 of the extraction tip. The fluidic pressure dispenses the dissolved analytes from the SPE tip 356 by directing the eluting solvent and dissolved analytes through the spray emitter 161 that has an applied voltage. As the eluting solvent and dissolved analytes are expelled from the nozzle sprayer 161, an electrospray (e.g., a mist of small droplets that can range from sub-micron size under nanoelectrospray conditions to about 1-10 µm across) is formed. The electrospray is typically generated at or near atmospheric pressure and provides highly charged droplets of the solution containing analytes. For example, microfabricated ESI chip 160 may include a 20×20 array of nozzle sprayer 161 (or an array of 5×5 nozzles or 7×7 nozzles or other similar arrangements of spray emitters in a microfluidic chip arrangement) having openings of between 2-50 µm in diameter (e.g., 2 µm, 5 µm, 10 µm, 30 µm or 50 µm in diameter). Other types of sprayers including a spray probe or tube devices and a microfabricated sprayer device can also be used.

Figure 5:
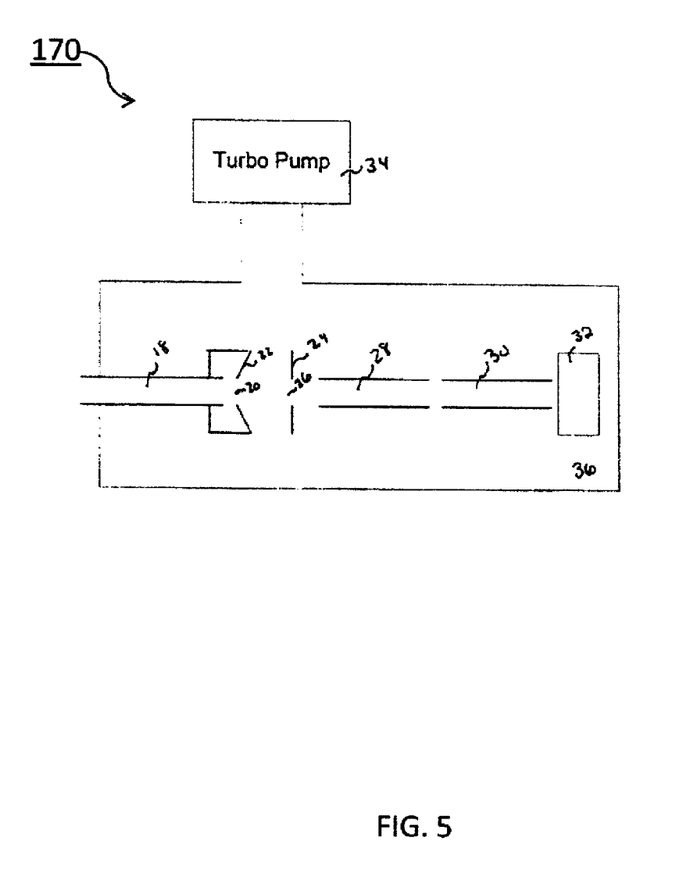
FIG. 5 shows a mass spectrometer.

Upon passage through the nozzle sprayer 161 the electrospray is directed towards the inlet orifice of an atmospheric pressure ionization (API) mass spectrometer 170. FIG. 5 shows a schematic representation of the components within mass spectrometer 170. The electrospray droplets enter into an atmospheric pressure interface (API), such as a capillary 18, that directs the ions from the electrospray into a vacuum portion 36 of the mass spectrometry system 170. As the droplets from the electrospray travel through the capillary 18, desolvation occurs such that ions emerge from an exit 20 of the capillary 18. The ions are directed through a skimmer 22 and the ions that emerge from the skimmer 22 are focused by a set of lenses 24 and into an ion optics region which may be a multipole region 28 or related or other type of lens focusing system. This multipole or ion optics region is typically operated in the Rf-only mode and may be composed of a quadrupole, hexapole, octapole or similar ion optics device. In embodiments in which a hexapole device is used as the multipole region 28, the ions are further guided through a quadrupole analyzer 30 or other mass analyzer capable of resolving ions with a mass-to-charge ratio and into a detector 32. The detector 32 amplifies the weak ion current signal of the sample ions. The detector may include an electron multiplier, photo multiplier or other suitable detector.

Figure 6:
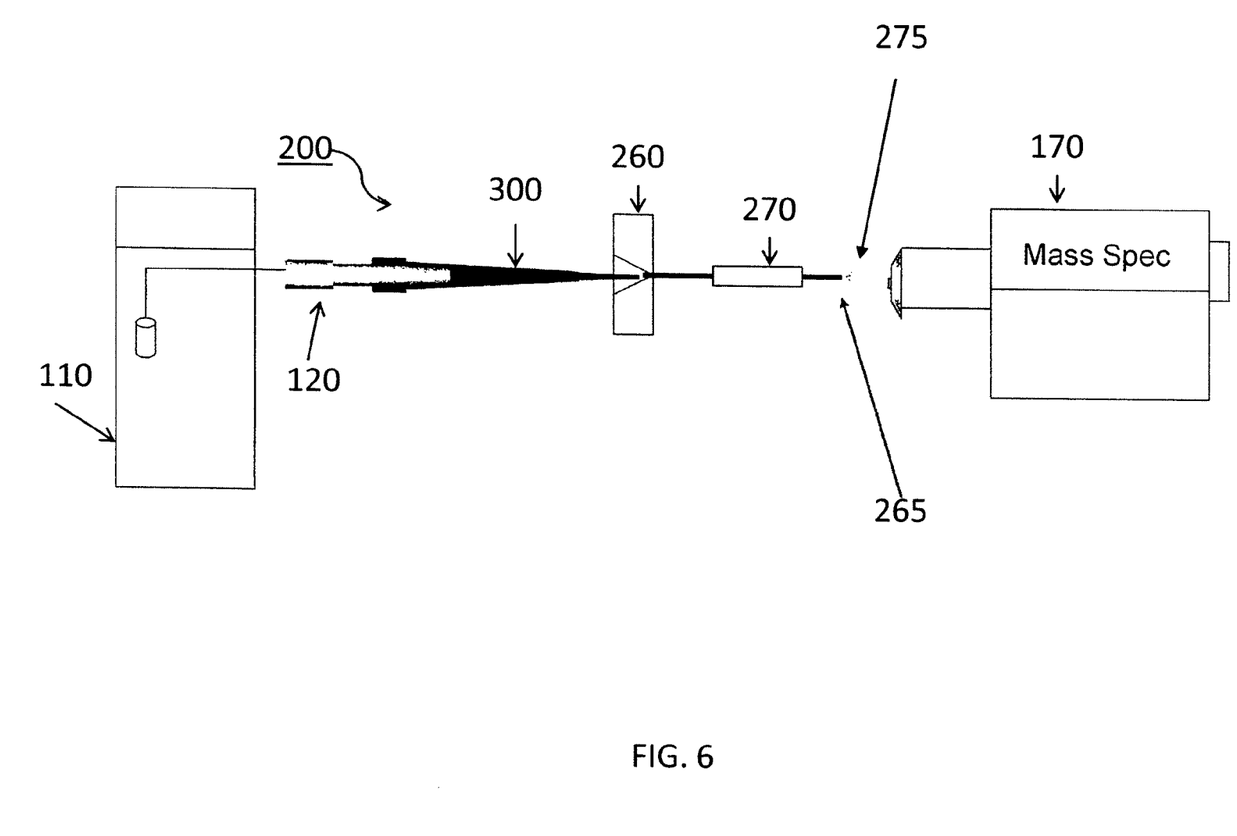
FIG. 6 shows a mass spectrometry system coupled with a solvent delivery system, an extraction tip system, and a sample introduction device.

In some embodiments, instead of using the microfabricated ESI chip 160, the analytes are eluted from the extraction tip 300 to a chromatographic column (such as a HPLC, Ultra Performance Liquid Chromatography (UPLC), micro HPLC, etc.). As shown in FIG. 6, in such embodiments, extraction tip 300 is connected to a loading block 260 which transfers or loads the effluent from the extraction tip 300 onto the chromatographic column 270. This loading block may be a modified, low-cost HPLC injector with a soft, leak-tight seal to accommodate the exit end 356 of the SPE tip, or a modified 'T' fitting with a similar soft insert seat on a side-arm of the T to allow insertion of the SPE tip into the side-arm to 'load' the sample from the SPE tip into the stream of mobile phase. In this embodiment eluting solvent from the extraction tip is 'loaded' via a flowing mobile phase of solvent onto, for example, a chromatographic column 270, to provide on-line liquid chromatograph/ mass spectrometry (LC/MS) or LC/MS/MS analyses via any API ion source.

Alternatively, as shown in FIG. 6, the API source sprayer may be a conventional ESI sprayer tube 265 as is commonly employed in ESI or APCI (atmospheric pressure chemical ionization) to produce a plume of vapor and droplets 275 for LC/MS and LC/MS/MS analyses. Systems 100 and 200 may produce ion mobility or mass spectral data which can be used for the qualitative or quantitative determination of chemicals/ analytes of a wide diversity of compound types.

In general, trace amounts of analytes, for example, in the range of parts per billion (ppb), or analytes having a concentration of nanograms per liter (ng/L) can be extracted and analyzed using the disclosed apparatus and methods. As described above, in some embodiments, the SPE packing materials and the eluting solvent can be a hydrophilic interaction liquid chromatography (HILIC) system. Solvents with high organic solvent content such as methanol and acetonitrile are suitable not only for eluting with a compatible stationary phase SPE packing material, but can also be used in electrospray. Examples of compatible stationary phase SPE in addition to HILIC includes reversed-phase stationary phases such as C-18, C-8, C-4, cyanopropyl, phenyl as well as polymer supports with similar stationary phases. In reversed-phase chromatography, an aqueous-organic eluting solvent is used in combination with a compatible stationary phase SPE. In addition to HILIC chromatographic packings, and uncoated silica may be used as a normal phase material for the stationary phase, such materials may be preferred for certain more polar analytes where highly organic solvents such as hexane and chlorinated solvents may be preferred as the mobile phase.

Figure 7:
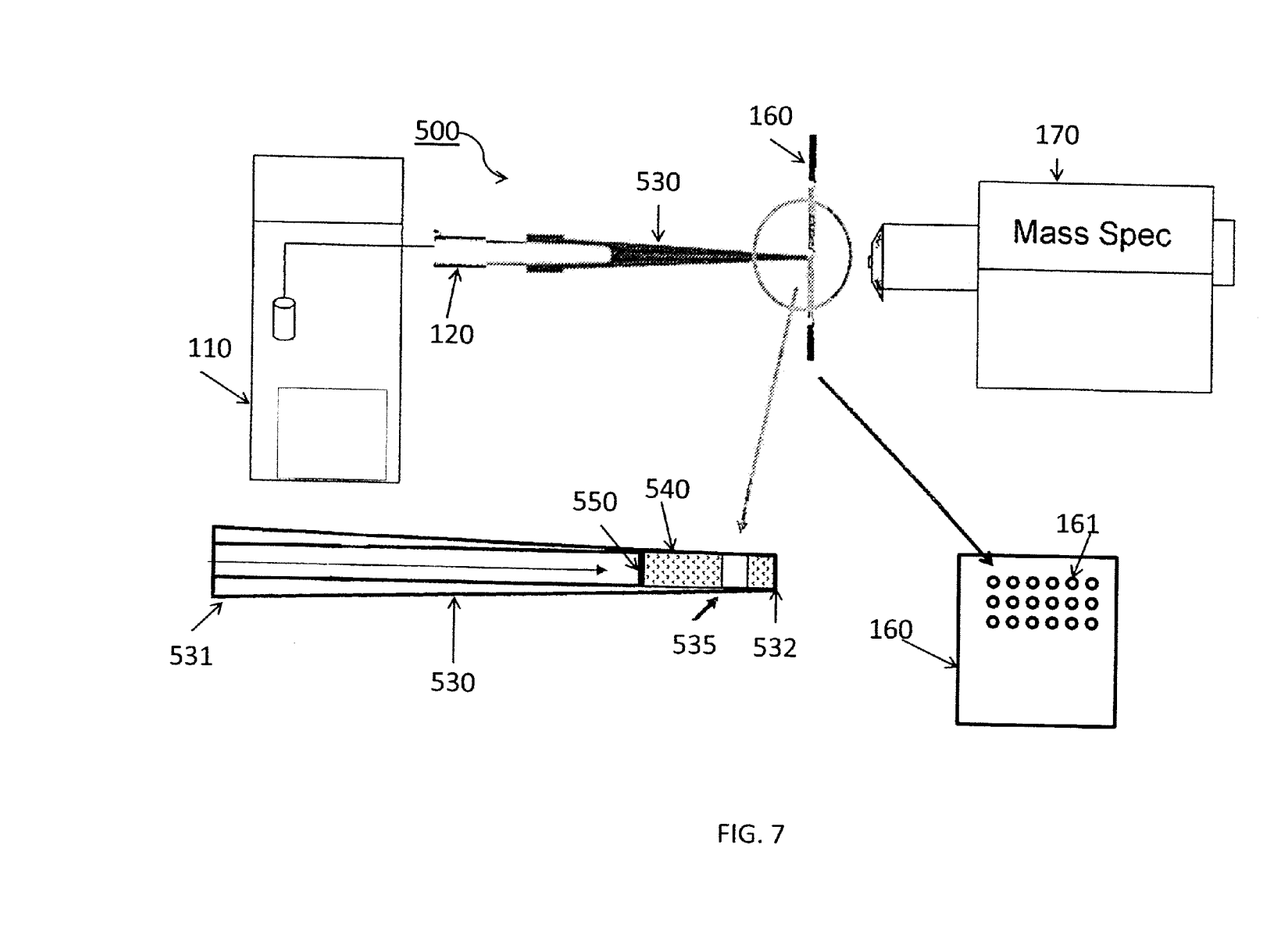
FIG. 7 shows a mass spectrometry system, and a microfluidic chip-based electrospray system.

As shown in FIG. 7, in alternative embodiments, a collected sample substrate 550, for example, a small (3-5 mm punched) portion of a DBS card, can be introduced into the larger diameter end 531 of an extraction (SPE) tip 530. In most cases it may be preferable to locate the punched DBS paper, as an example, all the way into the extraction tip 530 such that it rests securely in direct contact with the inlet surface of the SPE chromatographic packing 540. In some embodiments, the portion of the DBS card is cut or punched to a size that would allow the portion of the card to fit snuggly and/or mounted within the inner diameter when inserted near the SPE packing 540 within the extraction tip. A solvent from the solvent delivery 110 system enters the extraction tip and contacts the DBS card, dissolving analytes from the sample spot on the DBS card. The liquid (solvent and the dissolved analytes) containing the molecules of interest are driven under hydrostatic fluidic pressure into the SPE packing material 540 arranged near the end 532 of the extraction tip 530. The SPE packing material provides a stationary phase for the dissolved analytes to interact with during the chromatographic process. Depending on the physical and chemical characteristics of the dissolved analytes, different analytes experience different affinity towards the stationary phase. Analytes with higher affinity for the stationary phase would be retained nearer the portion of the SPE closer to the inlet end 531, while those analytes having lower affinity for the stationary phase would be less retained (if at all) in a portion of the SPE closer to end 532. In some cases, the analytes may remain in the mobile phase (e.g., the eluting solvent) as unretained components and be dispensed early in the elution process from the extraction tip. A region 535 depicts a representative 'band' of chemical migrating down the chromatographic column formed by the SPE packing material 540.

In some cases, the analytes retained by the SPE packing material can be subsequently separated from chemical interferences within the extracted sample. This concept is common in SPE techniques where a preferred strategy may be to achieve stronger retention of the chemical interferences than the analytes of interest. Thus as shown by the early elution of analyte band 535 in FIG. 7, the more highly retained chemical interferences may be retained on the SPE packing 540 while the analytes of interest elute first from the tip 532 for analysis. When the SPE tip is later discarded after the elution of the analytes of interest is complete, the chemical interferences which are retained in the SPE tip are also discarded thus minimizing problems associated with co elution of chemical components which contribute to matrix suppression of ionization, mixed mass spectra, reduced sensitivity, and contamination of the mass spectrometer detection system.

Following this interference elution step, a stronger elution solvent composed of higher percentages of organic solvents such as methanol, acetonitrile, etc. may be pumped through the SPE packing material to elute the analytes of interest to and through the microfabricated ESI chip 160 to effect sample clean up by solid-phase extraction. Thus the SPE technique affords a relative 'clean up' of the initially extracted sample by separating the unwanted chemical interferences within the original crude sample (e.g. from a tissue slice, dried blood spot, etc.) Alternatively, the sample may be eluted from the SPE packing material 540 via a gradient mobile phase (increasing percentage of the stronger, organic solvent which is common to reversed-phase HPLC techniques) to produce some chromatography. As described in reference to FIG. 4, extracted analytes can be transformed into ions at atmospheric pressure using microfabricated ESI chip 160 before the ions are analyzed by a mass spectrometer 170 to provide qualitative and quantitative information on the analytes originally contained in the collected sample.

In the example shown in FIG. 7, the tip 530 described above can additionally be used in systems in which eluting solvent and dissolved analytes from the collected sample substrate (e.g. a portion of a DBS card) is 'loaded' via a flowing mobile phase flow of solvent onto, for example, a chromatographic column 270, in FIG. 5 to provide on-line LC/MS or LC/MS/MS analyses via a suitable API ion source (e.g., systems similar to those described in relation to FIG. 6).

Methods that involve directly extracting analytes from a sample surface may offer increased sensitivity compared to eluting extracting analytes from a sample mounted within the extraction tip. The increase in sensitivity may be a result of the minimized dilution of analytes that get retained by the SPE packing material 530 when eluting a mounted sample within the extraction tip.

Figure 8:
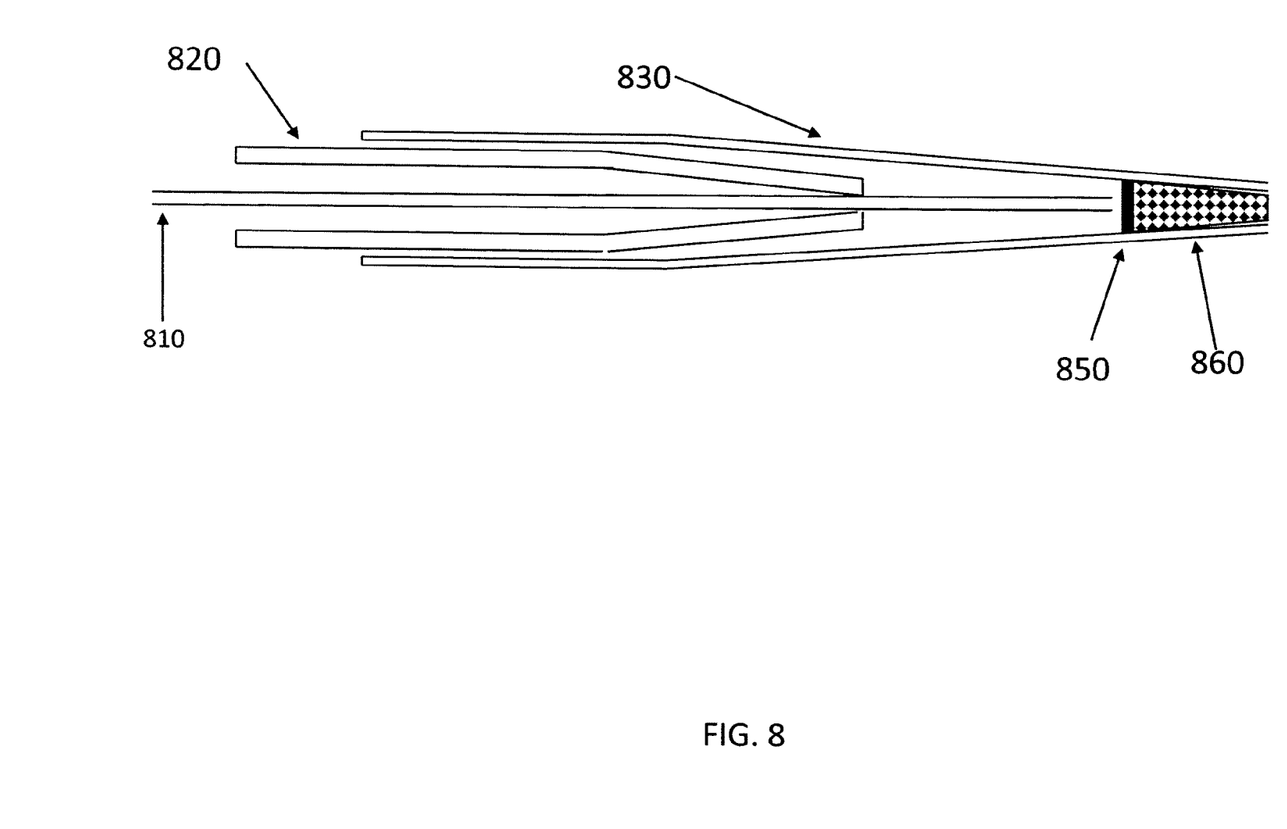
FIG. 8 shows a modified mandrel connected to an extraction tip

FIG. 8 shows a mandrel 820 adapted to connect with an extraction tip 830. The mandrel 820 positions and secures an inner capillary 810 that may be extended axially through the mandrel. By incorporating the inner capillary, the elution solvent can be directly delivered to a specific region of a sample 850 mounted within the extraction tip 830. By introducing the solvent to a specific region, less solvent is required because the volume of solvent introduced does not need to fill the larger end of the extraction tip 830 before contacting the sample. The direct delivery of solvent to the sample 850 will wet the sample and surround it with solvent for the elution/extraction process. The extracted analytes are then directed by the fluidic pressure to flow through the SPE packing The filling up of the larger end of the extraction tip shown in FIG. 7 may take more time (decreasing the sample throughput) and would also dilute the dissolved analytes contained in the elution solvent. A lower sensitivity may result from such dilution. As noted above, electrospray mass spectrometry is a concentration-sensitive technique that can be optimized by spraying a sample solution that is as concentrated with the analytes of interest as possible.

A variety of disposable, single use collection substrates can be used with the techniques described herein. Examples of these collection substrates include paper as commonly employed with dried blood spots (DBS), for example, in the Guthrie Card used for the analysis of DBS in newborn screening procedures, forensic testing, and bioanalytical testing, or any number of alternative small, disposable collection materials/substrates.

The collection substrate can also be a punched paper disk or disk of the sample/substrate material inside the extraction tip 530. The sample residue contained within the substrate medium may then be appropriately treated and/or eluted with suitable solvents either directly from the extraction tip 530 that contains SPE packing material 540 to a sprayer.

The one or more analytes eluted from the extraction tips may be ionized by either the electrospray, APCI or some of the recent open air ionization techniques which include, for example, direct analysis in real time (DART), desorption electrospray ionization (DESI) or atmospheric sampling automated probe (ASAP) processes and detected by any form of modern mass spectrometry to produce either full-scan mass spectra in either the positive ion mode or the negative ion mode depending upon the chemistry of the eluted analytes. Alternatively, the one or more detected analytes may be analyzed via other common mass spectrometric acquisition modes such as selected reaction monitoring (SRM), multiple reaction monitoring (MRM), selected ion monitoring (SIM) or other common modern acquisition modes of mass spectrometry including those capable of producing high resolution mass spectra such as FTMS, orbitraps, time-of-flight, etc. The disclosed apparatus and methods can be applied to clinical diagnostics such as the extraction and analysis of immunosuppressants, vitamin D and its analogs, amino acids, small drug compounds, antibiotics, peptides and proteins, inborn markers of metabolism such as carnitines, vitamins, forensic compounds, chemical warfare agents, nutritional supplements, biomarkers, small drug molecules and their metabolites, biologics, etc. In addition, the disclosed apparatus and methods can be used to directly extract analytes from the surface of a tissue slice or other biological samples residing in or on the surface of the sample.

A number of embodiments of the invention have been described. Nevertheless, it will be understood that various modifications may be made without departing from the spirit and scope of the invention.

What is claimed is:
1. A method comprising:
introducing a solvent into an extraction tip;
prior to extracting analytes from a dried blood spot card, causing the solvent to contact a solid phase extraction (SPE) or chromatographic packing material within the extraction tip;
extracting the analytes from the dried blood spot card by:
dispensing the solvent from a first end of the extraction tip to form a micro liquid junction that extends between the first end of the extraction tip and a surface of the dried blood spot card outside of the extraction tip;
allowing the solvent to dissolve the analytes from the dried blood spot card; and
aspirating the solvent and dissolved analytes into the extraction tip from the surface of the dried blood spot card through the first end of the extraction tip such that the analytes are retained in the SPE packing material in the extraction tip by applying a vacuum at a second end of the extraction tip;

interfacing the extraction tip to an automation device to deliver the extraction tip used to extract the analytes to an ion sprayer; and directing ions from the ion sprayer to a mass analyzer.

2. The method of claim 1, further comprising: repeating the steps of dispensing, applying and aspirating at different locations of the dried blood spot card.

3. The method of claim 1, further comprising: repeating the steps of dispensing, applying and aspirating at the same location on the dried blood spot card.

4. The method of claim 1, wherein the ion sprayer is an electrospray ionization source having multiple openings through which the extraction tip can singularly or in multiple deliver the analyte.

5. The method of claim 1, further comprising aligning the extraction tip to be in close proximity to the dried blood spot card.

6. The method of claim 1, wherein the first end of the extraction tip has a smaller diameter than the second end.

7. The method of claim 6, wherein a diameter of the first end is between 400 μm to 1200 μm and a diameter of the second end is between 1 to 10 mm.

8. The method of claim 1, wherein dispensing the solvent comprises dispensing microliters of solvent from the first end of the extraction tip to contact the dried blood spot card.

9. The method of claim 1, wherein the SPE packing material includes a material suitable for Hydrophilic Interaction Liquid Chromatography (HILIC).

10. The method of claim 9, wherein the solvent is a normal phase eluting solvent.

11. The method of claim 10, wherein the normal phase eluting solvent includes methanol or acetonitrile.

12. The method of claim 1, wherein the solvent is introduced into the extraction tip via the first end.

13. The method of claim 1, wherein aspirating the solvent and dissolved analytes into the extraction tip via the first end of the extraction tip comprises extracting multiple analytes from the dried blood spot card.

14. A method of extracting analytes from a sample, the method comprising:

cutting a dried blood spot card to generate portion of the card including the sample to fit within an inner diameter an extraction tip;

positioning the portion of the card including the sample within the extraction tip;

introducing a solvent to a first end of the extraction tip;

causing analytes within the sample to dissolve in the solvent;

causing the solvent to contact a solid phase extraction (SPE) packing material within the extraction tip;

eluting the analytes retained by the SPE packing material; and causing the dissolved analytes to exit the extraction tip from a second end of the extraction tip.

15. The method of claim 14, wherein the first end has a larger diameter than the second end.

* * * * *